US006973347B1

(12) United States Patent
Ben-Haim et al.

(10) Patent No.: US 6,973,347 B1
(45) Date of Patent: Dec. 6, 2005

(54) LOCAL CARDIAC MOTION CONTROL USING APPLIED ELECTRICAL SIGNALS AND MECHANICAL FORCE

(75) Inventors: Shlomo Ben-Haim, Cessaria (IL); Nissim Darvish, Haifa (IL); Yuval Mika, Zichron Yaakov (IL); Benny Rousso, Bat Yam (IL); Bella Felzen, Haifa (IL)

(73) Assignee: Impulse Dynamics NV, Curacao (AN)

( * ) Notice: Subject to any disclaimer, the term of this patent is extended or adjusted under 35 U.S.C. 154(b) by 0 days.

(21) Appl. No.: 09/979,937

(22) PCT Filed: May 25, 2000

(86) PCT No.: PCT/IL00/00303

§ 371 (c)(1),
(2), (4) Date: May 20, 2002

(87) PCT Pub. No.: WO00/72912

PCT Pub. Date: Dec. 7, 2000

Related U.S. Application Data

(63) Continuation-in-part of application No. 09/320,090, filed on May 26, 1999, now Pat. No. 6,442,424.

(51) Int. Cl.[7] .............................................. A61N 1/18
(52) U.S. Cl. ....................... 607/3; 607/2; 607/9; 600/16
(58) Field of Search ........................... 607/1–5, 16–17, 607/9, 36–38; 600/16–17

(56) References Cited

U.S. PATENT DOCUMENTS

| 3,572,345 | A | * | 3/1971 | Auphan | 607/129 |
|---|---|---|---|---|---|
| 3,587,567 | A | * | 6/1971 | Schiff | 601/21 |
| 5,468,254 | A | | 11/1995 | Hahn et al. | 607/5 |
| 5,540,722 | A | | 7/1996 | Clare et al. | 607/5 |
| 5,582,580 | A | * | 12/1996 | Buckman et al. | 601/41 |
| 5,584,803 | A | | 12/1996 | Stevens et al. | 604/6.16 |
| 5,651,378 | A | | 7/1997 | Matheny et al. | 128/898 |
| 5,674,259 | A | * | 10/1997 | Gray | 607/20 |
| 5,814,079 | A | | 9/1998 | Kieval | 607/4 |
| 5,913,876 | A | * | 6/1999 | Taylor et al. | 607/2 |
| 6,304,777 | B1 | | 10/2001 | Ben-Haim et al. | 607/2 |

FOREIGN PATENT DOCUMENTS

| WO | WO 97/25098 | 7/1997 | A61N 1/00 |
|---|---|---|---|
| WO | WO 98/10830 | 3/1998 | A61N 1/362 |
| WO | WO 98/10832 | 3/1998 | A61N 1/362 |

OTHER PUBLICATIONS

Hayashi, I. et al, "Right Vagal Nerve Stimulation During Minimally Invasive Direct Coronary Artery Bypass Grafting in Dogs: A Preliminary Study", *Journal of Cardiovascular Surgery* (Torino), 39:4, Aug. 1998, pp. 469-471.

(Continued)

*Primary Examiner*—Carl H. Layno
(74) *Attorney, Agent, or Firm*—William H. Dippert; Wolf, Block, Schorr & Solis-Cohen LLP

(57) ABSTRACT

Apparatus (18) for performing a medical procedure on a beating heart (20) includes a mechanical stabilization element (25), a surface (27) of which is adapted to be applied to a segment (24) of the heart to reduce motion of the segment. One or more electrodes (100) are fixed to the surface of the stabilization element, so as to contact the segment when the stabilization element is applied to the segment. Preferably, at least one of the one or more electrodes is adapted to apply electrical signals to the segment so as to further reduce motion thereof, while the heart continues to pump blood.

64 Claims, 5 Drawing Sheets

OTHER PUBLICATIONS http://www.medtronic.com/cardiac/mics/prod_clearview.html. Feb. 2002.

Coronary Artery Bypass Grafting without Cardiopulmonary Bypass and without Interruption of Native Cononary Flow Using a Novel Anastomosis Site Restraining Device ('Octopus'), by Borst, et al., Journal of the American College of Cardiology, 27(6), May 1996, pp. 1356-1364.

R.G. Matheny, et al., "Vagus Nerve Stimulation as a Method to Temporarily Slow or Arrest the Heart", Annual of Thoracic Surgery, 63(6) Published by Elsevier Science Inc. Jun. 1997.

W.R. Burfeind, et al., "The Effect of Mechanical Cardiac Stabilization on Left Ventricular Performance", European Journal of Cardio-Thoracic Surgery 14, 1998, pp. 285-289.

R.A. Malkin, et al., "AC Leakage Currents Cause Complete Hemodynamic Collapse Below the Venticular Fibrillation Threshold", 1999 Computers in Cardiology Annual Conference, Hannover, Germany, Sep. 1999.

C.D. Swerdlow, et al., "Cardiovascular Collapse Caused by Electrocardiographically Silent 60Hz Intracardiac Leakage Current: Implications for Electrical Safety" Circulation. 99(19),, pp. 2559-2564, May 18, 1999.

U.S. Appl. No. 09/260,769, entitled: "Contractility Enhancement Using Excitable Tissue Control and Multi-Site Pacing", filed Mar. 2, 1999.

U.S. Appl. No.: 60/136,092, entitled: "Shockless Defibrillation", filed May 26, 1999.

U.S. Appl. No.: 60/203,092, entitlled: "High-Frequency Induction of Cardioplegia", filed May 5, 2000.

* cited by examiner

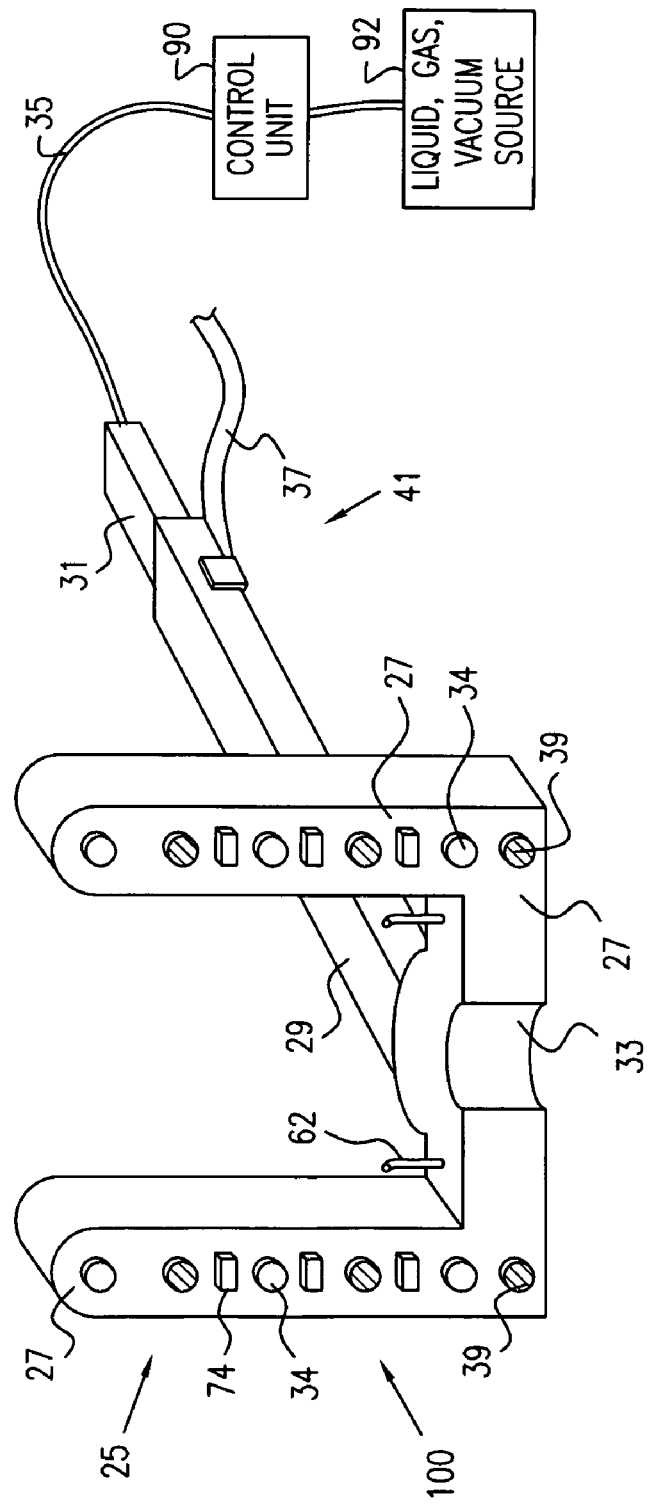

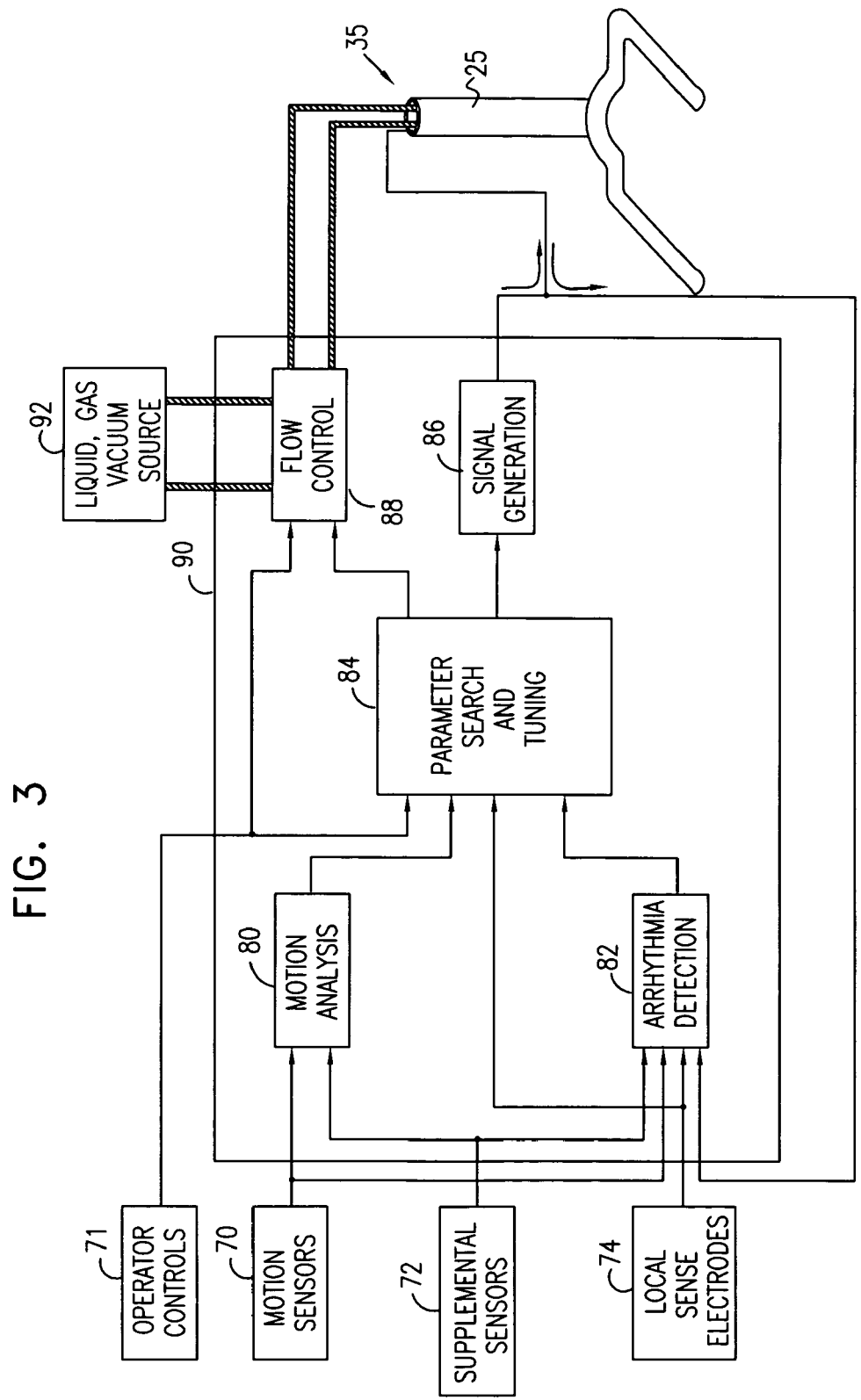

LOCAL CARDIAC MOTION CONTROL USING APPLIED ELECTRICAL SIGNALS AND MECHANICAL FORCE

CROSS-REFERENCE TO RELATED APPLICATIONS

This application is a continuation-in-part of U.S. patent application Ser. No. 09/320,090, entitled "Local cardiac motion control using applied electrical signals," filed May 26, 1999, now U.S. Pat. No. 6,442,424 which is assigned to the assignee of the present patent application and is incorporated herein by reference.

FIELD OF THE INVENTION

The present invention relates generally to invasive devices and methods for treatment of biological tissue, and specifically to devices and methods for controlling tissue and muscle during surgery.

BACKGROUND OF THE INVENTION

Heart surgery is often accompanied by the induction of cardioplegia (elective stopping of essentially all cardiac activity by injection of chemicals, selective hypothermia, mechanical stabilization, or electrical stimuli). In humans, induced global cardioplegia is nearly always practiced in conjunction with cardiopulmonary bypass.

Recently, minimally-invasive methods of cardiac surgery have been developed, in which the heart is approached through an incision made between the ribs, without sternotomy. It is sometimes preferred that, rather than inducing cardioplegia, the surgeon mechanically restrains a portion of the heart on which a surgical procedure, such as a bypass graft, is to be performed. Various tools and methods have been developed for this purpose, such as: (a) a suction cup-based stabilization platform (e.g., the Utrecht Octopus); (b) mechanical stabilization devices, such as the Ultima OPCAB System, produced by Guidant, Inc. (Indianapolis, Ind.); (c) the Octopus 2 or the EndoOctopus device, both produced by Medtronic, Inc. (Minneapolis, Minn.); (d) a U-shaped metal foot and other stabilizers produced by Genzyme Surgical Products, Inc. (Tucker, Ga.); (e) the Octopus Suction stabilizer, produced by Medtronic GmbH, Germany; and (f) CardioVations mechanical stabilizers produced by Ethicon Endo-Surgery (Cincinnati, Ohio).

The ClearView Blower/Mister, produced by Medtronic, is used during minimally-invasive cardiac surgery to spray a gas/saline mist into the operative field, so as to remove blood therefrom. The surgeon bends the device into a desired shape and places it near to the operative field, so that only the target area will be sprayed. In a product description on the World Wide Web (http://www.medtronic.com/cardiac/mics/prod_clearview.html, Feb. 8, 2000), Medtronic suggests that "generous tube length provides access to the surgical site, while the user's hand remains outside the surgical field."

An article entitled "Coronary artery bypass grafting without cardiopulmonary bypass and without interruption of native coronary flow using a novel anastomosis site restraining device ('Octopus')," by Borst et al., Journal of the American College of Cardiology, 27(6) (May 1996), pp. 1356–1364, which is incorporated herein by reference, describes use of the Octopus suction-generating device during experimental surgery on in situ pig hearts.

Such mechanical restraint of the heart muscle requires that substantial force, e.g., pressure or vacuum, be applied, which can cause tissue trauma. The effects of mechanical stabilization are described in an article, "The effects of mechanical stabilization on left ventricular performance," by Burfeind et al., European Journal of Cardio-Thoracic Surgery, 14(1998), pp. 285–289, which is incorporated herein by reference.

PCT Patent Publication WO 97/25098, to Ben-Haim et al., and the corresponding U.S. National Phase patent application Ser. No. 09/101,723, entitled, "Electrical muscle controller," which are assigned to the assignee of the present patent application and are incorporated herein by reference, describe methods for modifying the force of contraction of at least a portion of a heart chamber by applying a non-excitatory electrical signal to the heart at a delay after electrical activation of the portion. The signal may be applied in combination with a pacemaker or defibrillator, which also applies an excitatory signal (i.e., pacing or defibrillation pulses) to the heart muscle.

PCT Patent Publication WO 98/10832 to Ben-Haim et al., and the corresponding U.S. National Phase patent application Ser. No. 09/254,900, entitled, "Cardiac output enhanced pacemaker," which are also assigned to the assignee of the present patent application and incorporated herein by reference, describe a pacemaker that modifies cardiac output. This pacemaker applies both excitatory (pacing) and non-excitatory electrical signals to the heart. By applying non-excitatory signals of suitable strength, appropriately timed with respect to the heart's electrical activation, the contraction of selected segments of the heart muscle can be increased or decreased.

U.S. Pat. No. 5,651,378, to Matheny et al., and an article entitled, "Vagus Nerve Stimulation as a Method to Temporarily Slow or Arrest the Heart," by Matheny and Shaar, Annals of Thoracic Surgery, 63(6) Supplement (June 1997), pp. S28–29, which are both incorporated herein by reference, describe a method to stimulate the vagus nerve in order to slow or stop a patient's heart during coronary artery bypass grafting surgery. In addition, an article entitled "Right vagal nerve stimulation during minimally invasive direct coronary artery bypass grafting in dogs: A preliminary study," by Hayashi et al, Journal of Cardiovascular Surgery (Torino), 39(4) August 1998, pp. 469–471, which is incorporated herein by reference, describes a first set of experiments, in which the vagal nerve was stimulated so as to slow the heart rate. In a second set of experiments, the calcium channel blocking agents diltiazem or verapamil were administered in conjunction with the vagal nerve stimulation, and produced either marked bradycardia or ventricular arrest. It is noted that stimulation of the vagus nerve affects not only cardiac function, but also the functioning of other parts of the patient's body, such as the pharynx, larynx, trachea, lungs, and gastrointestinal tract.

SUMMARY OF THE INVENTION

It is an object of some aspects of the present invention to provide improved methods and apparatus for regulating the heart.

It is a further object of some aspects of the present invention to provide improved methods and apparatus for reducing motion of the heart during minimally-invasive and open-chest surgery.

It is yet a further object of some aspects of the present invention to provide improved methods and apparatus for applying mechanical force to reduce motion of the heart during minimally-invasive and open-chest surgery.

It is still a further object of some aspects of the present invention to provide improved methods and apparatus for reducing motion of the heart during minimally-invasive and open-chest surgery, while minimizing or substantially eliminating injury to the heart resulting from the motion reduction.

In preferred embodiments of the present invention, tissue control apparatus inhibits motion of a segment of a patient's heart, while allowing the heart to continue to pump blood. The tissue control apparatus comprises a stabilization element, which has a surface that is applied to the heart in order to reduce motion thereof. Additionally, one or more electrodes are coupled to the surface of the stabilization element. When the element is applied to the segment of the heart, a control unit applies electrical signals to the heart through at least one of the electrodes, so as to reduce or substantially stop motion of the segment for the duration of signal application. Alternatively or additionally, the signals are applied through the element so as to control other aspects of the mechanical behavior of the patient's heart. Further alternatively or additionally, the control unit detects electrical activity of the segment of the heart through the electrodes coupled to the stabilization element. At generally the same time, the stabilization element applies a mechanical motion-restraining force to the segment of the heart, so as to further reduce the segment's motion. Termination of signal and force application allows the segment, as well as the heart as a whole, to resume substantially normal motion.

The reduction in motion of the segment, as provided by these embodiments of the present invention, is typically used to enable a surgeon to perform minimally-invasive surgery or open-chest surgery, generally without inducing global cardioplegia or requiring cardiopulmonary bypass. For some applications, the electrical signals are used to reduce the force applied—and thus the injury produced—by the stabilization element, while maintaining a desired level of motion reduction. Purely mechanical stabilization devices known in the art, by contrast, reduce motion of a segment of the heart through application of a mechanical force to the delicate tissue of the heart that is considerably larger than that generated using these embodiments of the invention, and therefore risk damaging the tissue which is being forced to be substantially motionless.

In some preferred embodiments of the present invention, one or more motion sensors, e.g., accelerometers, are coupled to the stabilization element and/or to the heart, and send motion signals to the control unit indicative of the segment's motion and, optionally, of the motion of other areas of the heart. Preferably, the motion signals serve as feedback to enable the control unit to adjust the electrical signals applied to the heart, in order to reduce or otherwise regulate the detected motion of the segment. In a preferred embodiment, the control unit receives the motion signals from the sensors, and actuates the electrodes to apply the electrical signals in order to change contractility and/or contraction timing of muscle in the segment, so as to reduce the detected motion.

The electrical signals applied to the heart preferably comprise one or more of: regular pacing pulses, rapid pulses, a fencing signal (as described hereinbelow), and an enhancement signal The enhancement signal is typically similar to an Excitable-Tissue Control (ETC) signal, as described in the above-referenced PCT Patent Publication WO 97/25098, U.S. patent application Ser. No. 09/101,723, and in U.S. patent application Ser. No. 09/260,769, entitled "Contractility enhancement using excitable tissue control and multi-site pacing," which is assigned to the assignee of the present patent application and incorporated herein by reference. While for some applications these signals are applied so as to reduce motion of the heart, they may alternatively or additionally be applied to modify the mechanical behavior of the heart in other ways, such as those described in one or more of the patent applications incorporated herein by reference. Most preferably, the electrical signals are synchronized with the overall heartbeat, and have timing, shape, and magnitude characteristics which are determined during a calibration period of the control unit. As a result of calibration of the tissue control apparatus, a high degree of stabilization is preferably achieved, while maintaining adequate safety margins, e.g., acceptable patient vital signs, reduction in applied mechanical force, and avoidance of fibrillation and arrhythmia.

Generally, motion of the segment is characterized by a sum of: (a) a first component, consisting of motion resulting from general contraction and relaxation of the heart; and (b) a second component, consisting of local motion due to stimulation of the segment by the electrodes on the stabilization element, and due to the motion-restraining force generated by the stabilization element. It is a goal of this embodiment of the present invention to apply electrical signals which alter the second component, particularly with respect to the timing thereof, such that the net motion of the segment, resulting from summing the two components, is generally minimized and/or smoothed.

In some preferred embodiments of the present invention, additional electrodes are placed at multiple sites on the epicardium and/or endocardium of the segment of the heart. Alternatively or additionally, the additional electrodes are placed in blood vessels of the heart or in a vicinity of the heart, and, optionally, on areas of the heart other than the segment. Typically, each of the additional electrodes conveys a particular waveform to the heart, which may differ in certain aspects from the waveforms applied to other electrodes. The particular waveform to be applied to each electrode is preferably determined by the unit under the control or supervision of a human operator, in such a manner as to regulate the first and/or the second component of the segment's motion.

U.S. patent application Ser. No. 09/320,091, entitled, "Induction of cardioplegia using applied electrical signals," which is assigned to the assignee of the present invention and is incorporated herein by reference, describes methods for applying electrical signals to the heart to induce a global cardioplegic state. Additionally, the above-mentioned U.S. patent application Ser. No. 09/320,090 describes methods and apparatus for reducing the motion of a segment of the heart. Aspects of the methods described in these patent applications may also be used in conjunction with the principles of the present patent application. In particular, in a preferred embodiment of the present invention, the electrical signals applied to the heart comprise rapid pulses and/or fencing signals, as described hereinbelow, applied through one or more of the electrodes coupled to the stabilization element, in order to induce a state of generally constant and/or reduced contraction of the segment. The use of such pulses is described further in application Ser. Nos. 09/320,091 and 09/320,090. Additionally, the signals may be applied to other regions of the heart in order to modify contraction parameters in the other regions (e.g., timing and strength), such that motion of the segment is reduced. Alternatively or additionally, rapid pulses and/or other signals are applied using methods and apparatus described in a US patent application filed May 5, 2000, entitled "High-frequency induction of cardioplegia," which is assigned to the assignee of the present patent application and is incorporated herein by reference.

In some preferred embodiments of the present invention, a "fencing" signal is applied through one or more of the electrodes, preferably in order to prevent or inhibit the propagation of an action potential from one region of the heart to another. Fencing may be applied in conjunction with any (or none) of the electrical signals described hereinabove.

Most preferably, the fencing signal is applied in a vicinity of the segment. Such fencing is described in PCT Patent Publication WO 98/10830 and U.S. patent application Ser. No. 09/254,903, both of which are entitled, "Fencing of cardiac muscles," assigned to the assignee of the present invention, and incorporated herein by reference. Fencing is typically used, according to these embodiments, to reduce motion and/or a contraction force of the segment, generally by blocking or reducing the normal propagation of signals, and sometimes by applying the fencing signal to one or more sites within the segment.

In some preferred embodiments of the present invention, periods of mechanical force and electrical signal application are separated by periods in which force and/or electrical signals are not applied. Preferably, the durations of the application and non-application periods are set to maximize the surgeon's time for performing surgery, without unnecessarily extending the length of time in which free motion of the segment is limited. It is noted, however, that even in applications which utilize continuous application to the segment of a stabilizing force and/or motion-reduction signals, the level of functioning of the rest of the heart is expected to be generally sufficient to support systemic activity without the need for cardiopulmonary bypass.

For some applications, it may be desirable to partially (and, in some cases, significantly) reduce the overall output of the heart in order to attain a high degree of stabilization of the segment for a short time. Suitable methods of electrical control of the heart to reduce cardiac output are described in the above-mentioned U.S. patent application Ser. Nos. 09/101,723 and 09/254,900 and in PCT Patent Publications WO 97/25098 and WO 98/10832. It is emphasized that in these embodiments, as in most applications of the present invention, the patient's vital signs are preferably monitored substantially continuously.

In some preferred embodiments of the present invention, an automatic or semi-automatic feedback loop modifies the electrical signals applied to the heart, so as to optimize the segment's stabilization without undesirably changing measured physiological parameters, such as, for example, pCO2, pO2, Left Ventricular Pressure (LVP), ECG, and systemic blood pressure. Preferably, an abnormal value of any of these parameters triggers an alarm, responsive to which the operator and/or the control unit initiates an appropriate response. Further preferably, arrhythmia and fibrillation detection capabilities, as well as appropriate treatment protocols, are incorporated into the control unit.

Preferably, application of the mechanical force and electrical signals in accordance with the present invention stabilizes the segment within a very short period, typically about 1 second, and can maintain the segment's stability for prolonged periods. The heart typically returns to normal function within about 2 seconds of removal of the electrical signals.

There is therefore provided, in accordance with a preferred embodiment of the present invention, apparatus for performing a medical procedure on a beating heart, including:

a mechanical stabilization element, a surface of which is adapted to be applied to a segment of the heart to reduce motion of the segment; and one or more electrodes, fixed to the surface of the stabilization element, so as to contact the segment when the stabilization element is applied to the segment.

Preferably, at least one of the one or more electrodes is adapted to apply electrical signals to the segment so as to further reduce motion thereof, while the heart continues to pump blood.

In a preferred embodiment, the one or more electrodes include one or more local sense electrodes, and the apparatus includes a control unit, coupled to the local sense electrodes. Preferably, the local sense electrodes are adapted to convey to the control unit a current responsive to electrical activity of the heart, and the control unit is adapted to modify the electrical signals responsive to the conveyed current.

Alternatively or additionally, the at least one of the one or more electrodes is adapted to apply the signals so as to modify contraction of muscle tissue of the heart.

Preferably, the at least one of the one or more electrodes is adapted to apply the signals at a rate greater than about 5 Hz.

In a preferred embodiment, the at least one of the one or more electrodes includes two electrodes, which are adapted to concurrently apply to the segment respective first and second electric fields at respective first and second frequencies, so as to generate a field in the heart at a beat frequency of the first and second frequencies which reduces motion of the segment.

Alternatively or additionally, the at least one of the one or more electrodes is adapted to apply to the segment an electric field having a carrier frequency in excess of about 500 Hz, an amplitude of which electric field is modulated at a modulation frequency, so as to reduce motion of the segment.

In a preferred embodiment, the one or more electrodes include one or more fencing electrodes, which are adapted to apply a fencing signal to the heart so as to block propagation of an activation wave into the segment. Alternatively or additionally, the one or more electrodes include one or more fencing electrodes, which are adapted to apply a fencing signal to the heart so as to reduce a contraction force thereof.

Optionally, the one or more electrodes include one or more pacing electrodes, which are adapted to apply a pacing signal to the heart. Further optionally, the one or more electrodes include one or more enhancement electrodes, which are adapted to apply an enhancement signal to the heart. Still further optionally, the one or more electrodes include one or more local sense electrodes, which are adapted to sense electrical activity of the heart.

Typically, the one or more electrodes include at least one carbon electrode, stitch electrode, wire electrode, and/or needle electrode.

In a preferred embodiment, the apparatus includes a transport element, fixed to the stabilization element, which transport element is adapted to convey a fluid between the segment of the heart and the stabilization element, when the stabilization element is applied to the segment.

There is further provided, in accordance with a preferred embodiment of the present invention, a method for performing a medical procedure on a beating heart, including:

applying a mechanical stabilization element to a segment of the heart, so as to reduce motion of the segment; and
conveying electrical signals between the segment and the element.

Typically, performing the procedure includes performing a treatment on the segment while motion of the segment is reduced. Alternatively or additionally, performing the procedure includes performing a diagnostic procedure while motion of the segment is reduced.

Preferably, applying the signals includes applying bipolar and/or unipolar signals, as well as calibrating the signals intermittently during the procedure.

In a preferred embodiment, applying the signals includes:
applying a first signal, prior to performing the procedure, so as to precondition a response of the heart; and
applying a subsequent signal, during the procedure, so as to reduce the motion of the segment during the procedure.

Alternatively or additionally, applying the signals includes:
sensing electrical activity of the heart to detect arrhythmia thereof; and
applying electrical energy to the heart to treat the arrhythmia.

Further alternatively or additionally, applying the signals includes:
sensing electrical activity of the heart; and
modifying the application of the electrical signals responsive to the sensed electrical activity.

Preferably, the method includes sensing motion of the heart, wherein applying the signals includes modifying a characteristic of at least some of the signals applied to the heart responsive to the sensed motion.

In a preferred embodiment, applying the signals includes applying a fencing signal to the heart to block propagation of an activation wave into the segment of the heart and/or to reduce a contraction force thereof.

Typically, applying the signals includes applying the signals so as to further reduce motion of the segment.

In a preferred embodiment, applying the signals includes applying pulses at a rate greater than 5 Hz.

In a preferred embodiment, applying the electrical signals includes applying to the segment first and second electric fields at respective first and second frequencies, so as to generate a field in the heart at a beat frequency of the first and second frequencies which reduces motion of the segment. Alternatively or additionally, applying the electrical signals includes applying to the segment an electric field having a carrier frequency in excess of about 500 Hz, an amplitude of which electric field is modulated at a modulation frequency, so as to reduce motion of the segment.

Typically, applying the signals includes applying pulses and/or an enhancement signal to the segment.

In a preferred embodiment, applying the signals includes applying the signals so as to modify contraction of muscle tissue of the heart. Typically, modifying the contraction includes inducing contraction of the muscle tissue. Alternatively or additionally, applying the signals includes:
determining an aspect of the motion of the segment due generally to contraction of muscle tissue outside the segment; and
adjusting the signals responsive to the determined aspect of the segment's motion, so as to reduce the aspect of the segment's motion.

In a preferred embodiment, applying the signals includes applying signals through the stabilization element to a plurality of sites on the segment of the heart. For example, applying the signals may include applying a first waveform at a first one of the sites and applying a second waveform, which differs from the first waveform, at a second one of the sites. Preferably, applying the first and second waveforms includes controlling a timing relationship of the waveforms so as to reduce the motion of the segment.

There is still further provided, in accordance with a preferred embodiment of the present invention, apparatus for performing a medical procedure on a beating heart, including:
a stabilization element, a surface of which is adapted to be applied to a segment of the heart to reduce motion of the segment; and
one or more transport elements, fixed to the stabilization element, which are adapted to convey a fluid between the segment of the heart and the stabilization element, when the stabilization element is applied to the segment.

Preferably, one of the one or more transport elements is adapted to apply a liquid and/or gas to the segment of the heart.

Alternatively or additionally, one of the one or more transport elements is adapted to apply suction, so as to remove liquid from the surface of the heart.

There is yet further provided, in accordance with a preferred embodiment of the present invention, a method for performing a medical procedure on a beating heart, including:
applying a stabilization element to a segment of the heart, so as to reduce motion of the segment; and
conveying a fluid between the segment and the element, when the stabilization element is applied to the segment.

The present invention will be more fully understood from the following detailed description of the preferred embodiments thereof, taken together with the drawings, in which:

BRIEF DESCRIPTION OF THE DRAWINGS

FIG. 2A is a schematic illustration of the stabilization element, in accordance with a preferred embodiment of the present invention;

FIG. 3 is a schematic block diagram of a control unit, which generates signals to be applied to the heart through the stabilization element, in accordance with a preferred embodiment of the present invention.

DETAILED DESCRIPTION OF PREFERRED EMBODIMENTS

Figure 1:
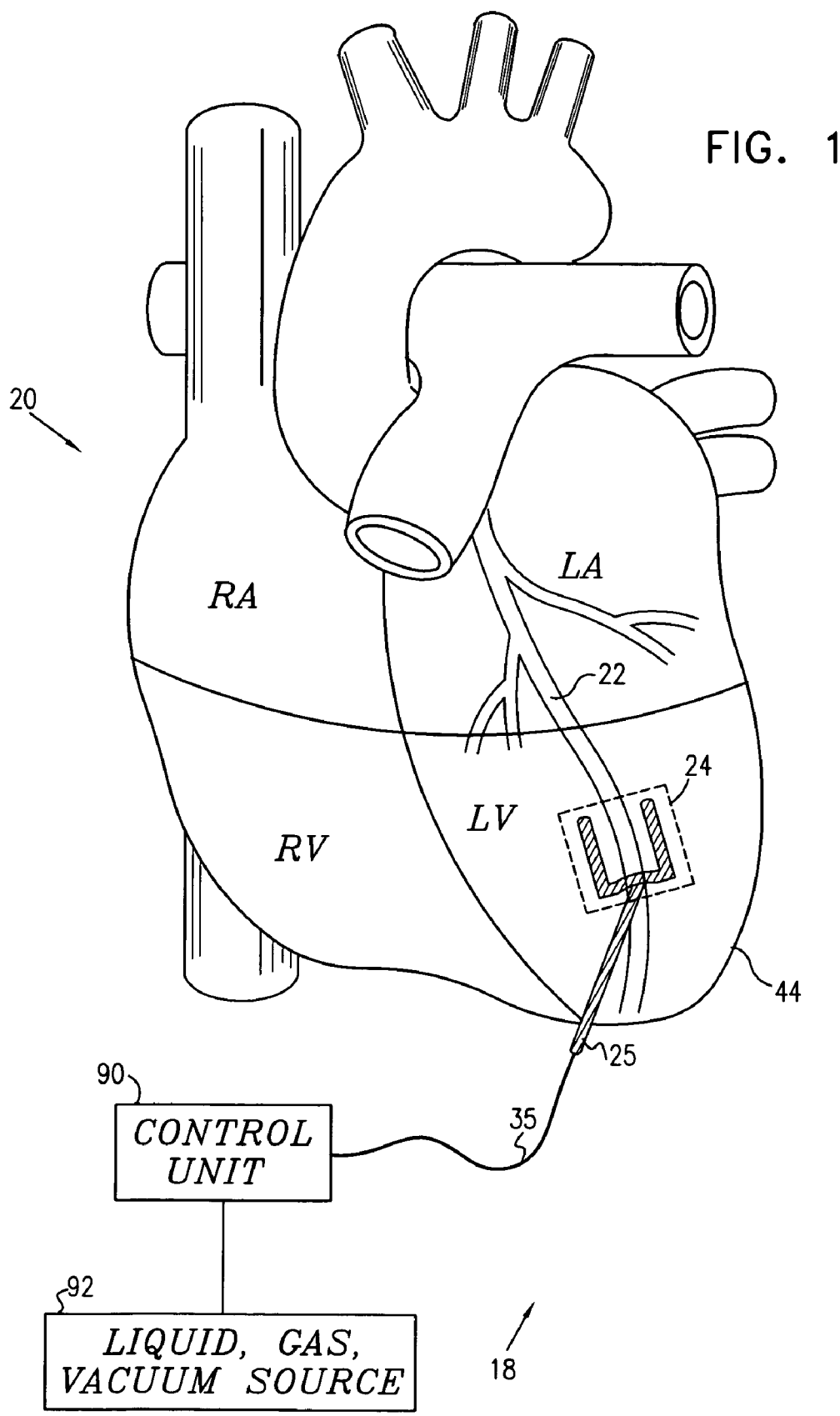
FIG. 1 is a schematic illustration of the external surface of a heart, showing the placement of a stabilization element thereon, in accordance with a preferred embodiment of the present invention.
Figure 2B:
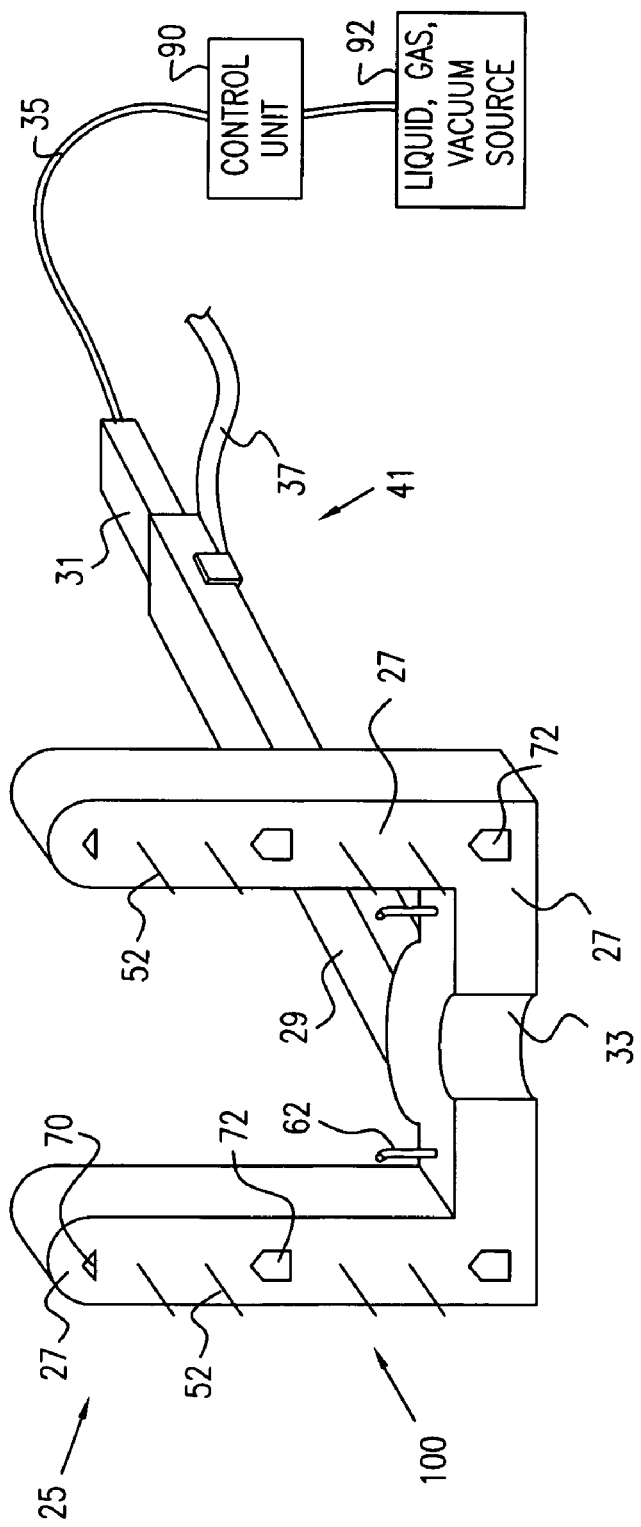
FIG. 2B is a schematic illustration of the stabilization element, in accordance with another preferred embodiment of the present invention.
Figure 2C:
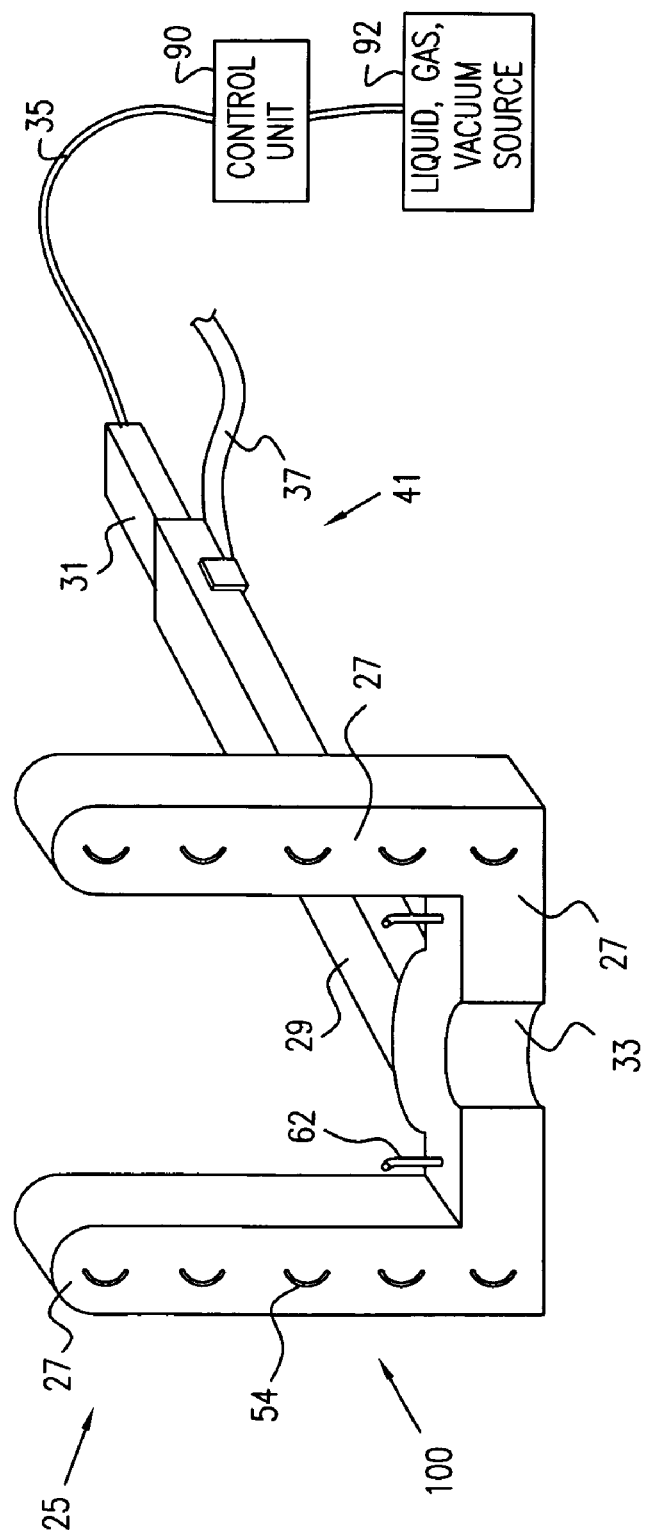
FIG. 2C is a schematic illustration of the stabilization element, in accordance with yet another preferred embodiment of the present invention.

Reference is made to FIGS. 1, 2A, 2B, and 2C. FIG. 1 is a schematic illustration of apparatus 18, comprising a stabilization element 25 for reducing the motion of a segment 24 of a patient's heart 20, in accordance with a preferred embodiment of the present invention. FIGS. 2A, 2B, and 2C are schematic illustrations of stabilization element 25, in respective configurations thereof, in accordance with preferred embodiments of the present invention. Two techniques are typically utilized concurrently to modulate the motion of segment 24, in order to enable surgery within the segment:

(1) Mechanical stabilization: A surface 27 of stabilization element 25 is placed on segment 24, so as to apply a mechanical force thereto. The force is typically derived from a positive pressure exerted by surface 27 of the element on heart 20. Alternatively or additionally, one or more optional vacuum ports 39 on surface 27 are coupled through a control unit 90 of apparatus 18 to a liquid-gas-vacuum source 92. The vacuum ports hold the surface of the heart in contact with the stabilization element, thereby reducing motion of segment 24. Typically, but not necessarily, surface 27 is roughened or otherwise configured so as to reduce or eliminate any slip between surface 27 and segment 24.

(2) Electrical stimulation and/or sensing: One or more electrodes 100 coupled to surface 27 are actuated by control unit 90 to apply electrical signals to heart 20 and/or to sense electrical activity of the heart. Preferred parameters of the signals are described hereinbelow with reference to FIG. 3. The electrical signals typically reduce motion of the heart, but may, alternatively or additionally, pace the heart or intermittently enhance or otherwise modulate motion of the heart.

Typically, application of signals as provided by these embodiments of the present invention enables the mechanical force applied by element 25 to be reduced compared to forces applied using strictly mechanical cardiac stabilizers known in the art. Moreover, the reduced mechanical force is generally achieved while maintaining at least the same level of motion reduction as is yielded using the prior art stabilizers. The inventors believe that reducing the applied force, as is enabled using these embodiments of the present invention, minimizes injury to tissue of the heart that may be produced using the prior art mechanical stabilizers. Additionally, use of mechanical stabilization in conjunction with the electrical signals may reduce motion of the segment to a level below that which could safely be attained by applying mechanical force or electrical signals separately.

Optionally, a handle 41 of stabilization element 25 has two members 29 and 31, which are slidably coupled to each other. Lines 35 preferably pass through handle 41, to couple control unit 90 to electrodes 100 and vacuum ports 39. For some applications, lines 35 couple additional electrodes, sensors, and actuated devices on the stabilization element to control unit 90. To simplify the performance of open-chest procedures, a connecting member 37 typically couples handle 41 to a chest retractor (not shown), so as to keep the stabilization element generally stationary with respect to the patient's chest.

An elevated portion 33 of stabilization element 25 preferably enables surface 27 of the element to be placed on segment 24, without directly compressing a particular site within the segment. Thus, for example, elevated portion 33 may be placed over the left anterior descending artery 22 of heart 20, so as not to restrict blood flow through the artery. Preferably, one or more liquid/gas transport elements 62 on elevated portion 33 or elsewhere on the stabilization element apply one or more materials, such as physiological saline solution, gaseous CO2, and/or air to the surface of heart 20, so as to keep the surgery site moist and/or clear of blood. Further preferably, the flow of these materials through transport elements 62 is regulated by control unit 90, which is coupled to control flow from liquid-gas-vacuum source 92. Alternatively or additionally, elements 62 apply suction to the surgery site, so as to remove therefrom blood or other liquids that may interfere with the surgeon's work.

In a preferred embodiment of the present invention, transport elements 62 are coupled to stabilization element 25 in the absence of electrodes coupled thereto. Prior art transport elements, such as the ClearView Blower/Mister described in the Background section of the present application, are entities unto themselves, which must be deliberately placed in the operative field, and subsequently maintained there, often by a person other than the surgeon. In this embodiment of the present invention, by contrast, transport elements 62 are coupled to the stabilization element, which will in any case be placed and maintained in the operative field (typically using connecting member 37).

Depending on the patient's condition and the site of the surgery, a surgeon will typically select a stabilization element in which electrodes 100 comprise one or more of the following types of electrodes: carbon electrodes 34 (FIG. 2A), needle electrodes 52 (FIG. 2B), or wire electrodes 54 (FIG. 2C). As appropriate, other types of electrodes may be incorporated into stabilization element 25, in addition to or instead of those shown. Alternatively or additionally, more or fewer electrodes may be incorporated into the stabilization element. In the preferred embodiment shown in FIG. 2A, for example, dedicated local sense electrodes 74 coupled to stabilization element 25 convey electrical signals to control unit 90 responsive to cardiac electric activity. Alternatively or additionally, some or all of electrodes 100 (FIGS. 2B and 2C) convey signals to the control unit responsive to the heart's electrical activity, without the use of dedicated local sense electrodes.

The types and placement of electrodes and sensors in FIGS. 2A, 2B, and 2C are shown by way of example. Other sites on stabilization element 25, or in and around the heart, are appropriate for electrode or sensor placement in other applications of the present invention. In particular, electrodes may be placed in a manner similar to that described in the above-mentioned U.S. patent application Ser. No. 09/320,090, entitled "Local cardiac motion control using applied electrical signals." Additionally, different numbers of electrodes or sensors (including no electrodes or sensors in some areas) and different types and combinations of sensors and coil, stitch, defibrillation, basket, screw, patch, needle and wire electrodes may be used in applying the principles of the present invention. It is noted that whereas specific types and placements of electrodes are described herein and shown in the figures, it is within the scope of the present invention to use, as appropriate, substantially any electrodes known in the art of tissue stimulation and bioelectrical sensing, and to place these electrodes on stabilization element 25, at one or more locations on or in a vicinity of the heart, or elsewhere on or in the patient's body.

In addition to the electrodes described hereinabove, a plurality of motion sensors 70 (e.g., accelerometers) and one or more optional supplemental sensors 72 are preferably coupled to stabilization element 25 (FIG. 2B), to the heart, or to another site on or in the patient's body. Sensors 72 may comprise, for example, a systemic blood pressure sensor, an LVP sensor, a pO2 sensor, a pCO2 sensor, a flow rate sensor, and/or a force sensor, which measures a contact force between stabilization element 25 and heart 20. The electrodes and sensors (optionally in combination with other electrodes and sensors not coupled to the stabilization element) provide substantially continuous monitoring of the patient's vital signs, in order to ensure that all of the signs are maintained within a safe range during the surgery. To the extent that any of the vital signs is outside the range, control unit 90 will either take corrective action on its own and/or provide an alarm to the surgeon, who will then be able to respond appropriately.

FIG. 3 is a schematic block diagram of control unit 90, which conveys electrical energy to stabilization element 25 in order to reduce motion of segment 24, in accordance with a preferred embodiment of the present invention. Alternatively or additionally, the control unit conveys to the stabilization element other forms of electrical energy, such as standard pacing pulses or the enhancement signal described in the Summary section of this application. Preferably, control unit 90 conveys the electrical energy to one or more of electrodes 100 coupled to surface 27 of stabilization element 25, in order to reduce or substantially stop the motion of segment 24. In a preferred embodiment, local sense electrodes 74 and/or electrodes 100 convey signals responsive to the electrical activity of heart 20 to the control unit, and substantially no signals are applied to the heart through the stabilization element.

Motion sensors 70, described hereinabove with reference to FIG. 2B, preferably send motion sensor signals to a motion analysis block 80 of control unit 90. The motion sensor signals provide feedback to the control unit, which modifies the electrical signals applied to the heart responsive thereto. For example, the electrical signals may include pulses, characteristics of which are adjusted by the control unit responsive to the motion sensor signals, in order to minimize motion of segment 24. Motion analysis block 80 preferably comprises amplifiers to amplify low-level signals generated by motion sensors 70, and a signal processing block, coupled to the amplifiers, which determines respective states of motion of the motion sensors. In some applications, motion analysis block 80 additionally receives signals from one or more of supplemental sensors 72, particularly those sensors that detect mechanical phenomena such as blood flow rate and blood pressure.

Preferably, motion analysis block 80 conveys results of its analysis to a "parameter search and tuning" block 84 of control unit 90, which iteratively modifies characteristics of the electrical signals in order to reduce the motion of segment 24. To achieve this goal, block 84 typically utilizes multivariate optimization and control methods known in the art (e.g., downhill simplex, linear state variable feedback or extended Kalman filters), in order to cause the measured motion and/or other parameters to converge to a desired value. For the purposes of some embodiments of the present invention, block 84 modifies a set of controllable parameters to minimize and/or smooth motion of segment 24. Preferably, the controllable parameters are conveyed by block 84 to a signal generation block 86 of control unit 90, which generates, responsive to the parameters, electrical signals that are applied by electrodes 100 to segment 24.

As described hereinabove, motion sensors 70 are generally attached to stabilization element 25 and/or directly to the heart. Typically, the motion sensors are mechanically coupled to segment 24, and the element is placed adjacent to a surgical location within the segment. In the embodiment shown in FIG. 1, for example, the stabilization element is placed on the surface of left ventricle 44, adjacent to the left anterior descending artery 22, to enable a single-vessel coronary artery bypass graft to be performed thereon. Alternatively, the stabilization element is placed at another ventricular site, or, for some applications, at an atrial site of heart 20. Typically, the control unit receives motion signals from sensors 70 indicative of motion of the surgical site, and actuates electrodes 100 to apply the electrical signals in order to cause muscle in a vicinity of the site to contract in a manner which generally reduces motion of the site.

Generally, motion of segment 24 is characterized by a sum of: (a) a first component, consisting of global heart motion resulting from beating of heart 20, and especially motion due to contraction of heart regions not within segment 24; and (b) a second component, consisting of motion resulting from the part of the heart in segment 24 that is typically stimulated by electrodes 100. Control unit 90 generally applies the electrical energy to electrodes 100 on the stabilization element so as to alter the second component of the motion. In a preferred embodiment, additional electrodes (not shown) are applied directly to the heart, independent of stabilization element 25. These additional electrodes apply other signals to the rest of the heart, so as to alter the first component (and, particularly, to alter timing of the first component), such that the net motion of segment 24, resulting from summing the two components, is generally minimized and/or smoothed. Electrodes suitable for direct placement on the heart are described in the above-mentioned U.S. patent application Ser. No. 09/320,090, entitled "Local cardiac motion control using applied electrical signals."

Preferably, the electrical signals provided by some embodiments of the present invention have some similarity to pacing pulses, and/or are timed to correlate with pacing pulses. They are typically synchronized with the overall heartbeat, and have timing, shape, and magnitude characteristics which are determined during a calibration period at the beginning of a surgical procedure and/or at regular intervals during the procedure. For some applications, the electrical signals applied to the heart comprise combinations of signals described herein, including regular pacing, rapid pulses, fencing, enhancement signals and other signals.

During the calibration period, parameter search and tuning block 84 preferably executes an optimization algorithm, such as "gradient descent," in which, for example, block 84 modifies a characteristic (e.g., timing, duration, or magnitude) of the electrical signals generated by one of the electrodes described herein, and then determines whether the measured motion of segment 24 decreases, or changes in some other desired way, following the modification. Typically, in a series of similar calibration steps, block 84 modifies characteristics of the electrical signals applied by each of the other electrodes, wherein those modifications that reduce motion of segment 24 are generally maintained, and modifications that increase the motion of the segment are eliminated or avoided. In combination with the application of limited mechanical force by stabilization element 25, motion of segment 24 is gradually reduced to a point at which the surgeon can safely and conveniently perform the surgical procedure. Optionally, the surgeon does not use the stabilization element to apply mechanical force until motion of segment 24 has already been substantially reduced through the application of the electrical signals.

In some cases, it is desirable to have a preconditioning period of segment 24 and/or of the whole heart. During the preconditioning period, electrodes 100 (or other electrodes placed on the heart) apply the electrical signals for short periods initially, followed by progressively longer periods. During the preconditioning period, characteristics of the heart's response to the signals change, so that substantially similar inputs will engender different responses before and after the preconditioning period. In a preferred embodiment, the control unit applies signals for a 2 second period, followed by 4 second, 6 second, and longer periods, until a desired motion-reduction period of 20 seconds is attained. It is believed that the heart is preconditioned, or trained, during this period, and that training the heart during the preconditioning period may improve the response of the heart during subsequent signal-application periods. Because the heart may change its response to the applied signals throughout the surgical procedure, i.e., it is continually being trained, it is generally preferable to repeat the calibration at intermittent times during the procedure.

Most preferably, during the calibration period and during regular operation of control unit 90, an arrhythmia detection block 82 of control unit 90 receives inputs from motion sensors 70, supplemental sensors 72, electrodes 74 and 100, and/or other electrodes and sensors (not shown), and evaluates these inputs to detect an onset of cardiac arrhythmia. Preferably, block 82 employs techniques known in the art for determining arrhythmia, so that control unit 90 can treat or terminate the arrhythmia by pacing or by performing cardioversion or defibrillation. In a preferred embodiment, control unit 90 applies a shockless defibrillation technique, as described in U.S. Provisional Patent Application 60/136,092, entitled "Shockless defibrillation," which is assigned to the assignee of the present patent application and is incorporated herein by reference.

As described hereinabove, the motion sensor signals typically provide feedback to enable the control unit to modify the electrical signals applied to the heart, in order to reduce the detected motion of the segment. Additionally or alternatively, local sense electrodes 74, which optionally comprise some or all of electrodes 100, convey electrical signals to control unit 90 to enable parameter search and tuning block 84 to synchronize the electrical signals applied by electrodes 100 with the natural electrical activity of the heart and with propagation characteristics of the applied electrical signals. Preferably, parameter search and tuning block 84 assesses the output from local sense electrodes 74 in conjunction with the motion sensor signals, so as to determine appropriate parameters for the applied electrical signals, which both minimize motion of segment 24 and preserve the overall function of heart 20.

In a preferred embodiment of the present invention, some of electrodes 100 apply rapid pulses to segment 24 which are generally similar in form and intensity to pulses commonly used to pace the heart. The pulses are believed to induce a reversible state of generally constant contraction of the segment, without causing fibrillation or other dangerous arrhythmic activity. In a preferred rapid pulse application mode, control unit 90 generates a regularly-spaced series of current pulses, injecting current through the electrodes into underlying cardiac tissue. In this mode, the pulses are preferably characterized by a frequency above 5 Hz, and are typically applied above 10 Hz. Pulses applied between about 25 and 30 Hz have been found by the inventors to produce generally desirable results. Other parameters typically characterizing the pulses include a duty cycle between about 5 and 50%, a DC offset between about −10 and +10 mA, and an amplitude between about −20 and +20 mA. An amplitude of between about 1 and 5 mA is typically sufficient. These values are cited by way of example, however, and it will be understood that higher or lower frequencies and amplitudes may also be used, depending on the type and placement of the electrodes and on the specific condition of the patient's heart. For example, a frequency higher than 100 Hz was tested on rabbits and found to yield suitable results.

Alternatively or additionally, control unit 90 applies a fencing signal to some of electrodes 100 (or to other electrodes, not coupled to the stabilization element), generally in order to inhibit the generation and propagation of an action potential from one region of the heart to another. Fencing is typically used in these applications to block or reduce the normal propagation of signals and/or to reduce the contractility of affected muscle tissue. Alternatively or additionally, the fencing signal generally reduces the contraction strength of the muscle stimulated thereby.

In a preferred embodiment, the electrical signals comprise first and second electrical signals, which are respectively applied to first and second sets of electrodes 100.

Preferably, the first and second signals have respective first and second frequencies associated therewith, which generate electric fields in the heart at the respective frequencies. Typically, the first and second signals have frequencies between about 500 and 20,000 Hz, and the difference between the first and second frequencies is between about 4 and 25 Hz. It is believed that the segment's motion is reduced responsive to a beat frequency generated by interference of the first and second signals. Suitable methods and apparatus for applying the first and second signals, mutatis mutandis, are described in the above-mentioned US patent application, entitled "High-frequency induction of cardioplegia."

Alternatively or additionally, the electrical signals applied by stabilization element 25 to segment 24 comprise an amplitude-modulated (AM) signal, applied by control unit 90 to one or more of electrodes 100. The AM signal comprises (a) a high-frequency component, usually over 500 Hz, which generally passes through cardiac tissue, substantially without affecting cardiac function, and (b) a low-frequency component, generated by modulation of the amplitude of the high-frequency component. The low-frequency, similar to the beat frequency described above, is preferably between about 4 and 25 Hz. Preferably, the AM signal is applied in a manner generally similar to that described in the application "High-frequency induction of cardioplegia."

In general, each one of electrodes 100 conveys a particular waveform to heart 20, differing in certain aspects from the waveforms applied by the other electrodes. The particular waveform to be applied is determined by control unit 90, preferably under the control of a human operator. Aspects of the waveforms which are set by the control unit, and may differ from electrode to electrode, typically include parameters such as time shifts between application of waveforms at different electrodes, waveform shapes, amplitudes, DC offsets, durations, frequencies, duty cycles, etc. For example, although the waveforms applied to the electrodes typically comprise a series of monophasic square wave pulses, other waveforms, such as a sinusoid, a series of uniphasic and/or biphasic square waves, or substantially any other shape known in the art of applying electric signals to tissue, could be used in the framework of the present invention. Additionally, in some operational modes, the voltage applied by some or all of electrodes 100 is controlled, rather than the current, as described hereinabove.

Generally, the shape, magnitude, and timing of the waveforms are optimized for each patient, using suitable optimization algorithms, as are known in the art, in order to attain a desired level of stabilization of segment 24. Typically, the optimization is performed continually, both during the calibration period and during regular operation. However, during a surgical procedure, the operational parameters are typically changed more gradually, so as not to interrupt the surgeon's actions.

Preferably, application of the electrical signals in accordance with the present invention increases the stability of segment 24 within a very short period (e.g., several seconds), such that the surgeon preferably applies mechanical force via stabilization element 25 to the segment when the segment is already at least partially stabilized. In this manner, a lower amount of mechanical force is typically applied to the segment than would be applied using prior art methods. It is believed that the lower force is likely to induce substantially less trauma to the heart compared with results obtained using prior art methods for cardiac mechanical stabilization. The inventors have found that the heart typically returns to normal function within about 2 seconds of removal of the electrical signals. A short waiting time, typically about 15 seconds, is preferably followed by recalibration before signals are applied again. Although the initial calibration period can take several minutes in order to determine appropriate signals to be applied by electrodes 100, recalibration typically requires less time. The method of this embodiment of the present invention has been found to be generally spontaneously reversible, typically without requiring cardioversion or defibrillation. (Cardioversion and defibrillation capabilities are nevertheless typically provided to enhance safety.)

Control unit 90 preferably comprises a flow control block 88, typically including valves and mechanical switches. Block 88 allows the control unit to regulate the flow of liquid and gas from source 92 to the surface of heart 20, as described hereinabove, and, additionally, to control the timing and/or strength of the vacuum applied through ports 39. Depending on the nature of the surgical procedure, the operation of flow control block 88 may be regulated directly by operator controls 71 and/or by parameter search and tuning block 84, responsive to the inputs thereto. In another preferred embodiment (not shown), the strength of the vacuum and/or the flow of liquid and gas to the heart is regulated independent of the control unit.

Although preferred embodiments are described hereinabove with reference to reducing motion of the segment of the heart in order to enable surgery on the segment, it will be understood that the present invention may be used for other purposes, such as to enhance a physician's ability to perform diagnostic tests on the segment. Furthermore, the principles of the present invention are applicable not only to the heart, but also to controlling local motion in segments of other types of tissue, such as smooth muscle (e.g., the intestines) and skeletal muscle.

It will be appreciated by persons skilled in the art that the present invention is not limited to what has been particularly shown and described hereinabove. Rather, the scope of the present invention includes both combinations and subcombinations of the various features described hereinabove and in the articles, patents and patent applications incorporated herein by reference, as well as variations and modifications thereof that are not in the prior art, which would occur to persons skilled in the art upon reading the foregoing description.

What is claimed is:

1. Apparatus for use during performance of a surgical procedure on a segment of a beating heart, comprising a surgical tool, which comprises:
    a mechanical stabilization element, a surface of which is adapted to be applied, during the surgical procedure, to the segment of the heart to reduce motion of the segment; and
    one or more electrodes, fixed to the surface of the stabilization element, so as to contact the segment when the stabilization element is applied to the segment.

2. Apparatus according to claim 1, wherein at least one of the one or more electrodes is adapted to apply electrical signals to the segment so as to further reduce the motion thereof, while the heart continues to pump blood.

3. Apparatus according to claim 2, wherein the one or more electrodes comprise one or more local sense electrodes, wherein the apparatus comprises a control unit, coupled to the local sense electrodes, wherein the local sense electrodes are adapted to convey to the control unit a current responsive to electrical activity of the heart, and wherein the control unit is adapted to modify the electrical signals responsive to the conveyed current.

4. Apparatus according to claim 2, wherein the at least one of the one or more electrodes is adapted to apply the signals so as to modify contraction of muscle tissue of the heart.

5. Apparatus according to claim 2, wherein the at least one of the one or more electrodes is adapted to apply the signals at a rate greater than about 5 Hz.

6. Apparatus according to claim 2, wherein the at least one of the one or more electrodes includes two electrodes, which are adapted to concurrently apply to the segment respective first and second electric fields at respective first and second frequencies, so as to generate a field in the heart at a beat frequency of the first and second frequencies which reduces the motion of the segment.

7. Apparatus according to claim 2, wherein the at least one of the one or more electrodes is adapted to apply to the segment an electric field having a carrier frequency in excess of about 500 Hz, an amplitude of which electric field is modulated at a modulation frequency, so as to reduce the motion of the segment.

8. Apparatus according to claim 2, wherein the at least one of the one or more electrodes is adapted to apply the electrical signals to the segment so as to substantially stop the motion of the segment, while the heart continues to pump blood.

9. Apparatus according to claim 2, wherein the one or more electrodes comprise one or more fencing electrodes, which are adapted to apply a fencing signal to the heart so as to block propagation of an activation wave into the segment.

10. Apparatus according to claim 2, wherein the one or more electrodes comprise one or more fencing electrodes, which are adapted to apply a fencing signal to the heart so as to reduce a contraction force thereof.

11. Apparatus according to claim 2, wherein the one or more electrodes comprise one or more pacing electrodes, which are adapted to apply a pacing signal to the heart.

12. Apparatus according to claim 2, wherein the one or more electrodes comprise one or more enhancement electrodes, which are adapted to apply an enhancement signal to the heart.

13. Apparatus according to claim 2, and comprising a transport element, fixed to the stabilization element, which transport element is adapted to convey a fluid between the segment of the heart and the stabilization element, when the stabilization element is applied to the segment.

14. Apparatus according to claim 1, wherein the one or more electrodes comprise one or more fencing electrodes, which are adapted to apply a fencing signal to the heart so as to block propagation of an activation wave into the segment.

15. Apparatus according to claim 1, wherein the one or more electrodes comprise one or more fencing electrodes, which are adapted to apply a fencing signal to the heart so as to reduce a contraction force thereof.

16. Apparatus according to claim 1, wherein the one or more electrodes comprise one or more pacing electrodes, which are adapted to apply a pacing signal to the heart.

17. Apparatus according to claim 1, wherein the one or more electrodes comprise one or more enhancement electrodes, which are adapted to apply an enhancement signal to the heart.

18. Apparatus according to claim 1, wherein the one or more electrodes comprise one or more local sense electrodes, which are adapted to sense electrical activity of the heart.

19. Apparatus according to claim 1, wherein the one or more electrodes comprise at least one carbon electrode.

20. Apparatus according to claim 1, wherein the one or more electrodes comprise at least one stitch electrode.

21. Apparatus according to claim 1, wherein the one or more electrodes comprise at least one wire electrode.

22. Apparatus according to claim 1, wherein the one or more electrodes comprise at least one needle electrode.

23. Apparatus according to claim 1, and comprising a transport element, fixed to the stabilization element, which transport element is adapted to convey a fluid between the segment of the heart and the stabilization element, when the stabilization element is applied to the segment.

24. A method for use during performance of a surgical procedure on a segment of a beating heart, comprising:
during the surgical procedure, applying a mechanical motion-restraining force to the segment of the heart, using a mechanical stabilization element so as to reduce motion of the segment;
conveying electrical signals between the segment and the element during the surgical procedure; and
terminating the applying of the mechanical motion-restraining force and the conveying of the electrical signals, so as to allow the segment to resume substantially normal motion.

25. A method according to claim 24, wherein conveying the electrical signals comprises receiving the electrical signals responsive to electrical activity of the heart.

26. A method according to claim 24, and comprising conveying a fluid between the stabilization element and the segment of the heart.

27. A method according to claim 24, wherein conveying the electrical signals comprises applying the electrical signals to the segment through the stabilization element.

28. A method according to claim 27, wherein applying the signals comprises applying bipolar signals.

29. A method according to claim 27, wherein applying the signals comprises applying unipolar signals.

30. A method according to claim 27, wherein applying the signals comprises calibrating the signals intermittently during the surgical procedure.

31. A method according to claim 27, wherein applying the signals comprises:
sensing electrical activity of the heart to detect arrhythmia thereof; and
applying electrical energy to the heart to treat the arrhythmia.

32. A method according to claim 27, wherein applying the signals comprises:
sensing electrical activity of the heart; and
modifying the application of the electrical signals responsive to the sensed electrical activity.

33. A method according to claim 27, and comprising sensing motion of the heart, wherein applying the signals comprises modifying a characteristic of at least some of the signals applied to the heart responsive to the sensed motion.

34. A method according to claim 27, wherein applying the signals comprises applying a fencing signal to the heart to block propagation of an activation wave into the segment of the heart.

35. A method according to claim 27, wherein applying the signals comprises applying a fencing signal in a vicinity of the segment to reduce a contraction force thereof.

36. A method according to claim 27, wherein applying the signals comprises applying pulses at a rate greater than about 5 Hz.

37. A method according to claim 27, wherein applying the electrical signals comprises applying to the segment first and second electric fields at respective first and second frequencies, so as to generate a field in the heart at a beat frequency of the first and second frequencies which reduces the motion of the segment.

38. A method according to claim 27, wherein applying the electrical signals comprises applying to the segment an electric field having a carrier frequency in excess of about 500 Hz, an amplitude of which electric field is modulated at a modulation frequency, so as to reduce the motion of the segment.

39. A method according to claim 27, wherein applying the signals comprises applying pulses to the segment.

40. A method according to claim 27, wherein applying the signals comprises applying an enhancement signal to the segment.

41. A method according to claim 27, wherein applying the signals comprises applying the signals so as to modify contraction of muscle tissue of the heart.

42. A method according to claim 41, wherein modifying the contraction comprises inducing contraction of the muscle tissue.

43. A method according to claim 41, wherein applying the signals comprises:
determining an aspect of the motion of the segment due generally to contraction of muscle tissue outside the segment; and
adjusting the signals responsive to the determined aspect of the segment's motion, so as to reduce the aspect of the segment's motion.

44. A method according to claim 27, wherein applying the signals comprises applying signals through the stabilization element to a plurality of sites on the segment of the heart.

45. A method according to claim 44, wherein applying the signals comprises applying a first waveform at a first one of the sites and applying a second waveform, which differs from the first waveform, at a second one of the sites.

46. A method according to claim 45, wherein applying the first and second waveforms comprises controlling a timing relationship of the waveforms so as to reduce the motion of the segment.

47. A method according to claim 27, and comprising:
during a preconditioning period, preconditioning a response of the heart by applying a first signal,
wherein applying the signals comprises applying a subsequent signal after the preconditioning period.

48. A method according to claim 27, wherein applying the signals comprises applying the signals so as to further reduce the motion of the segment, while the heart continues to pump blood.

49. A method according to claim 48, wherein applying the signals comprises applying the signals so as to substantially stop the motion of the segment, while the heart continues to pump blood.

50. A method according to claim 48, wherein applying the mechanical motion-restraining force comprises applying the mechanical motion-restraining force after the segment has been at least partially stabilized by applying the signals.

51. A method according to claim 48, and comprising conveying a fluid between the stabilization element and the segment of the heart.

52. A method according to claim 48, wherein applying the signals comprises applying a fencing signal to the heart to block propagation of an activation wave into the segment of the heart.

53. A method according to claim 48, wherein applying the signals comprises applying a fencing signal in a vicinity of the segment to reduce a contraction force thereof.

54. A method according to claim 48, wherein applying the electrical signals comprises applying to the segment first and second electric fields at respective first and second frequencies, so as to generate a field in the heart at a beat frequency of the first and second frequencies which reduces the motion of the segment.

55. A method according to claim 48, wherein applying the electrical signals comprises applying to the segment an electric field having a carrier frequency in excess of about 500 Hz, an amplitude of which electric field is modulated at a modulation frequency, so as to reduce the motion of the segment.

56. A method according to claim 48, wherein applying the signals comprises applying an enhancement signal to the segment.

57. Apparatus for performing a medical procedure on a beating heart, comprising:
    a stabilization element, a surface of which is adapted to be applied to a segment of the heart to reduce motion of the segment; and
    one or more transport elements, fixed to the stabilization element, which are adapted to convey a fluid between the segment of the heart and the stabilization element, when the stabilization element is applied to the segment.

58. Apparatus according to claim 57, wherein one of the one or more transport elements is adapted to apply a liquid to the segment of the heart.

59. Apparatus according to claim 57, wherein one of the one or more transport elements is adapted to apply a gas to the segment of the heart.

60. Apparatus according to claim 57, wherein one of the one or more transport elements is adapted to apply suction, so as to remove liquid from the surface of the heart.

61. A method for performing a medical procedure on a beating heart, comprising:
    applying a stabilization element to a segment of the heart, so as to reduce motion of the segment; and
    conveying a fluid between the segment and the element, when the stabilization element is applied to the segment.

62. A method according to claim 61, wherein conveying the fluid comprises applying a gas to the segment of the heart.

63. A method according to claim 61, wherein conveying the fluid comprises applying a liquid to the segment of the heart.

64. A method according to claim 61, wherein conveying the fluid comprises applying suction, so as to remove liquid from the surface of the heart.

* * * * *